United States Patent

Quagliato et al.

Patent Number: 5,840,764
Date of Patent: Nov. 24, 1998

[54] SUBSTITUTED HYDROXY-ANILINO DERIVATIVES OF CYCLOBUTENE-3,4-DIONES

[75] Inventors: Dominick A. Quagliato, Bridgewater, N.J.; Edward M. Matelan, Yardley, Pa.; Madelene M. Antane, Lawrenceville, N.J.

[73] Assignee: American Home Products Corporation, Madison, N.J.

[21] Appl. No.: 7,335

[22] Filed: Jan. 14, 1998

Related U.S. Application Data

[60] Provisional application No. 60/036,992 Jan. 30, 1997.

[51] Int. Cl.[6] ............ A01N 33/02; A01N 33/06; C07C 51/16; C07C 211/00
[52] U.S. Cl. ............ 514/646; 558/418; 558/419; 558/421; 558/422; 564/306
[58] Field of Search ............ 558/418, 419, 558/421, 422; 514/646; 564/306

[56] References Cited

U.S. PATENT DOCUMENTS

| | | | |
|---|---|---|---|
| 4,390,701 | 6/1983 | Algieri et al. | 546/235 |
| 4,673,747 | 6/1987 | Nobara et al. | 546/334 |
| 5,240,946 | 8/1993 | Kinney et al. | 514/364 |
| 5,354,746 | 10/1994 | Chandrakumar et al. | 514/211 |
| 5,397,790 | 3/1995 | Butera et al. | 514/310 |
| 5,401,753 | 3/1995 | Butera et al. | 514/311 |
| 5,403,853 | 4/1995 | Butera et al. | 514/399 |
| 5,403,854 | 4/1995 | Butera et al. | 514/415 |
| 5,464,867 | 11/1995 | Antane et al. | 514/524 |
| 5,466,712 | 11/1995 | Butera et al. | 514/524 |
| 5,506,252 | 4/1996 | Butera et al. | |

FOREIGN PATENT DOCUMENTS

| | | |
|---|---|---|
| 426379 | 10/1990 | European Pat. Off. . |
| 496561 | 1/1992 | European Pat. Off. . |

OTHER PUBLICATIONS

Tietze et al., Chem. Berg., 1991, 124, 1215–1221.
Tietze et al., Bioconjugate Chem., 1991, 2, 148–153.
Ehrhardt et al., Chem. Ber., 1977, 110, 2506–2523.
Neuse et al., Liebigs Ann. Chem., 1973, 619–632.
Takeno et al., Public Patent Disclosure Bull. No. 6–92915 (Japan).
Kinney et al., J.Med. Chem. 1992, 35, 4720.

*Primary Examiner*—Dwayne C. Jones
*Attorney, Agent, or Firm*—Rebecca R. Barrett

[57] ABSTRACT

The compound of the formula:

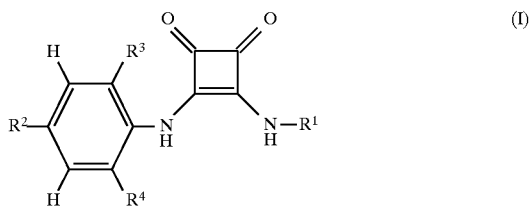

wherein $R^1$ is straight chain alkyl, branched chain alkyl, cycloalkyl, hydroxyalkyl, fluoroalkyl, or polyfluoroalkyl; and one of $R^2$, $R^3$ and $R^4$ is hydroxyl and the other two are, independently, H, CN, halogen, alkyl or hydroxyl; or a pharmaceutically acceptable salt thereof, is useful as a smooth muscle relaxant.

13 Claims, No Drawings

SUBSTITUTED HYDROXY-ANILINO DERIVATIVES OF CYCLOBUTENE-3,4-DIONES

BACKGROUND OF INVENTION

This application claims the benefit of U.S. Provisional Application No. 60/036,992, filed Jan. 30, 1997.

The present invention relates to novel 1,2-diamino derivatives of cyclobutene 3,4-diones having pharmacological activity, to a process for their preparation, to pharmaceutical compositions containing them and to their use, via potassium channel modulation, in the treatment of disorders associated with smooth muscle contraction. Such disorders include, but are not limited to, urinary incontinence, hypertension, asthma, premature labor, irritable bowel syndrome, congestive heart failure, angina and cerebral vascular disease.

Stemp et al. (EP-426379) disclose a class of amino substituted cyclobutenedione derivatives of chromans described as having blood pressure lowering activity and bronchodilatory activity. Takeno et al. (Public Patent Disclosure Bulletin No. 6-92915) report a series of diaminocyclobuten-3,4-diones. Our own efforts in this area have been disclosed in the following U.S. Pat. Nos. 5,464,867, 5,466,712, 5,403,853, 5,403,854, 5,397,790, and 5,401,753. Several series of 1-amino-2-phenylalkylamino-cyclobutene-3,4-diones are reported as H-2 receptor antagonists by Algieri et al. in U.S. Pat. No. 4,390,701. Several related 1-amino-2-phenoxyalkylamino derivatives are disclosed by Nohara et al. in U.S. Pat. No. 4,673,747. Additionally, U.S. Pat. No. 5,240,946 and EP-496561 disclose diaminocyclobuten-3,4-diones useful as NMDA antagonists.

The syntheses of variously substituted 1,2-diamino-cyclobutene-3,4-diones are described in the following publications: Tietze et al., Chem. Ber. 1991, 124, 1215; Tietze et al., Bioconjugate Chem. 1991, 2, 148; Ehrhardt et al., Chem. Ber. 1977, 110, 2506, Neuse et al., Liebigs Ann. Chem. 1973, 619, Ried et al., Liebigs Ann. Chem. 1973, 619, Kinney et al., J. Med. Chem. 1992, 35, 4702.

DESCRIPTION OF THE INVENTION

In accordance with the present invention there is provided a group of compounds of the formula (I):

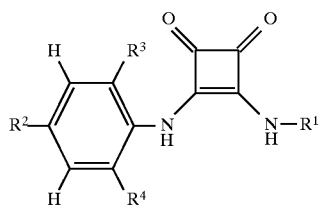

wherein:

$R^1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

and one of $R^2$, $R^3$ and $R^4$ is hydroxyl and the other two are, independently, H, CN, halogen, alkyl of 1 to 3 carbon atoms or hydroxyl;

or a pharmaceutically acceptable salt thereof.

A preferred aspect of this invention involves those compounds which have demonstrated activity at a concentration of less than 10.0 µM in the relaxation of smooth muscle represented by formula (I) wherein:

$R^1$ is straight chain alkyl of 1 to 10 carbon atoms, branched chain alkyl of 3 to 10 carbon atoms or fluoroalkyl of 1 to 10 carbon atoms;

and one of $R^2$, $R^3$ and $R^4$ is hydroxyl and the other two are, independently, H, CN, halogen, alkyl of 1 to 3 carbon atoms or hydroxyl;

or a pharmaceutically acceptable salt thereof.

It is understood that the definition of the compounds of formula (I), when $R_1$ contains an asymmetric carbon atom, encompasses all possible stereoisomers and mixtures thereof which possess the activity discussed below. In particular, it encompasses racemic modifications and any optical isomers which possess the indicated activity. Optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic and similarly known acceptable acids. Throughout this specification, reference to branched chain alkyl groups may include such groups as α,α-substituted branched chain alkyl in which the carbon atom adjacent to the nitrogen is tertiary, such as t-butyl, 1,1-dimethylpropyl, 3-methyl-3-pentyl, 3-ethyl-3-pentyl, 2,3-dimethyl-2-butyl, 2,3,3-trimethyl-2-butyl, 2,3-dimethyl-3-pentyl, and any similarly substituted branched alkyl chain.

The present invention also provides a process for the preparation of a compound of formula (I). More particularly, the compounds of formula (I) may be prepared by reacting a compound of formula (II):

wherein X and X' is a suitably designed leaving group such as methoxy, ethoxy, butoxy, isopropoxy, halogeno or a similar leaving group, with a compound of formula (III):

wherein Ar is the substituted phenyl ring shown hereinbefore or a group of atoms convertible thereto, followed by treatment with a compound of formula (IV):

wherein $R^1$ is as defined hereinbefore or a group of atoms convertible thereto, in a solvent such as ethanol, acetonitrile, or the appropriate amine (IV) at ambient or elevated temperature. Dichloromethane can be used as a cosolvent. The order of addition of the compound of formula (III) and the compound of formula (IV) to the compound of formula (II) may be reversed.

As mentioned previously, the compounds of formula (I) have been found to relax smooth muscle. They are active at concentrations below 10.0 µM. They are useful in the treatment of disorders associated with smooth muscle contraction, disorders involving excessive smooth muscle contraction of the urinary tract (such as incontinence), or of the gastrointestinal tract (such as irritable bowel syndrome), asthma, and hair loss. Furthermore, the compounds of formula (I) are potassium channel activators which render them useful for treatment of peripheral vascular disease, hypertension, congestive heart failure, stroke, anxiety, cerebral anoxia and other neurodegenerative disorders. The present invention provides a method of treating smooth muscle disorders in mammals including man, which comprises administering to the afflicted mammal an effective amount of a compound or a pharmaceutical composition of the invention.

The present invention also provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patient suffering from heart failure.

In order to obtain consistency of administration, it is preferred that a composition of the invention is in the form of a unit dose. Suitable unit dose forms include tablets, capsules, powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The following examples are presented to illustrate rather than limit the scope of the invention.

EXAMPLE 1

3-(Tert-butylamino)-4-(2-hydroxy-4-cyanophenyl)amino-3-cyclobutene-1,2-dione

A mixture of 3-methoxy-4-nitrobenzonitrile (1.5 g, 0.008 mol) and LiCl (1.07 g, 0.025 mol) in DMF (14 ml) was heated to reflux. The reaction is monitored by TLC (1:1 hexane: ethyl acetate). When the starting material has disappeared (approximately 3 hours), the reaction is cooled and 42 ml of 2.5N NaOH is added. The solution is extracted with diethyl ether. The aqueous layer is acidified with 73 ml of 2N HCl, then extracted well with ethyl acetate. The organic layer is washed with brine, dried ($Na_2SO_4$), and filtered. Concentration on a rotary evaporator yields 3-hydroxy-4-nitrobenzonitrile N,N-dimethylformyl hemiacetal. This product is passed through a pad of silica gel (2:1 ethyl acetate:hexane) to yield 3-hydroxy-4-nitrobenzonitrile, 1.31 g (0.00798 mol, 94.75%).

$^1$H NMR: δ, DMSO 7.4 (1H,s), 7.6 (1H,d, J 8.34), 8 (1H, d, J 8.59), 12 (1H,s)

MS: (EI) [m+]@m/z 164

A parr bottle was charged with palladium on activated carbon (5%, 0.204 g). A solution of 3-hydroxy-4-nitrobenzonitrile (1.36 g, 0.00829 mol) in 41 ml of ethanol was added. The reaction mixture was placed under 25 psi of hydrogen gas and shaken for 1 hour. TLC (1:1 hexane:ethyl acetate) shows that no starting material remained. The mixture was filtered through Celite® and evaporated to yield 3-hydroxy-4-aminobenzonitrile, 1.08 g (0.00806 mol, 97%).

MS: [(-)ESI][m-H]$^-$@m/z 133

A solution of 3-hydroxy-4-aminobenzonitrile (1.08 g, 0.008 mol) and diethyl squarate (1.19 ml, 0.008 mol) in dry ethanol (22 ml) was heated at 85° C. for two days. During the course of the reaction, a tan precipitate forms. TLC (1:1 hexane:ethyl acetate) indicates that no starting material is present. The solid is filtered through a Buchner funnel, washed with cold ethanol, and collected to give 3-ethoxy-4-(2-hydroxy-4-cyanophenyl)amino-3-cyclobutene-1,2-dione, 1.19 g (0.0046 mol, 57%).

$^1$H NMR: δ, DMSO 1.2 (3H, t, J 7.1), 4.38 (2H, q, J 7.1), 7.09 (1H, dd, J 1.8, 15.2),7.1 (1H, d, J 1.9), 7.2 (1H, d, J 8.3), 10.05 (1H, bs), 11.4 (1H, bs)

MS: [(-)ESI][m-H]$^-$@m/z 257

A mixture of 3-ethoxy-4-(2-hydroxy-4-cyanophenyl)amino-3-cyclobutene-1,2-dione (0.395 g, 0.0015 mol) and tert-butylamine (4 ml, 0.038 mol) in enough $CH_2Cl_2$ to form a solution (a small amount of dry ethanol was required) was stirred at room temperature for two days. During this time, a precipitate forms. TLC (2:1 ethyl acetate:hexane) indicates a loss of starting material. The reaction is evaporated to a solid on a rotary evaporator. The solid is taken up in ethyl acetate and extracted well with 0.25N HCl. The organic layer is washed once with distilled water, dried ($Na_2SO_4$), and evaporated to a solid. The solid is collected and washed with diethyl ether to give 3-(tert-butylamino)-4-(2-hydroxy-4-cyanophenyl)amino-3-cyclobutene-1,2-dione, 0.270 g (0.00095 mol, 62%).

$^1$H NMR: δDMSO 1.4 (9H, s), 7.13 (1H, d, J 1.75), 7.25 (1H, d, J 1.75), 8.0 (1H, d, J 8.34), 8.7 (1H,bs), 9.5 (1H, bs), 11.0 (1H, bs)

MS: (EI) m+@m/z 285

EXAMPLE 2

3-(Tert-amylamino)-4-(2-hydroxy-4-cyanophenyl)amino-3-cyclobutene-1,2-dione

A mixture of 3-ethoxy-4-(2-hydroxy-4-cyanophenyl)amino-3-cyclobutene-1,2-dione (0.395 g, 0.0015 mol) and tert-amylamine (4 ml, 0.034 mol) in enough $CH_2Cl_2$ to form a solution (a small amount of dry ethanol was required) was stirred at room temperature for two days. During this time, a precipitate forms. TLC (2:1 ethyl acetate:hexane) indicates a loss of starting material. The reaction is evaporated to a solid on a rotary evaporator. The solid is taken up in ethyl acetate and extracted well with 0.25N HCl. The organic layer is washed once with distilled water, dried ($Na_2SO_4$), and evaporated to a solid. The solid is collected and washed with diethyl ether to give 3-(tert-amylamino)-4-(2-hydroxy-4-cyanophenyl)amino-3-cyclobutene-1,2-dione, 0.253 g (0.00085 mol, 55%).

$^1$H NMR: δDMSO 0.85 (3H, t, J 7.5), 1.35 (6H, s), 1.73 (2H, q, J 7.2, 7.5), 7.14 (1H, d, J 1.76), 7.27 (1H, dd,J 1.76, 6.6), 7.97 (1H, d, J 8.35), 8.56 (1H, bs), 9.57 (1H, bs), 10.99 (1H, bs)

MS: (EI) m+@m/z 299

EXAMPLE 3

3-(2,2,1-Trimethylpropylamino)-4-(2-hydroxy-4-cyanophenyl)amino-3-cyclobutene-1,2-dione A mixture of 3-ethoxy-4-(2-hydroxy-4-cyanophenyl)amino-3-cyclobutene-1,2-dione (0.395 g, 0.0015 mol) and (R)-2,2,1-trimethylpropylamine (0.2M in ethanol, 23 ml, 0.0046 mol) was stirred at room temperature for two days. TLC (2:1 ethyl acetate:hexane) indicates a loss of starting material. The ethanol is evaporated on a rotary evaporator. The reaction is taken up in ethyl acetate and extracted well with 0.25N HCl. The organic layer is washed once with distilled water, dried ($Na_2SO_4$), and evaporated to a solid. The solid is collected and washed with diethyl ether to give 3-[(R)-2,2,1-trimethylpropylamino]-4-(2-hydroxy-4-cyanophenyl)amino-3-cyclobutene-1,2-dione, 0.345 g (0.00095 mol, 72%).

$^1$H NMR: δDMSO 0.90 (9H, s), 1.16 (3H, d, J 6.8), 4.02 (1H, dq, J 14.17,6.81, 3.08), 7.13 (1H, d, J 8.35), 7.26 (1H, dd, J 1.76, 6.59), 8.04 (1H, d, J 8.35), 9.48 (1H, bs), 11.0 (1H, bs)

MS: (EI) m+@m/z 313

EXAMPLE 4

3-(2,2,1-Trimethylpropylamino)-4-(2-hydroxy-6-cyanophenyl)amino-3-cyclobutene-1,2-dione A mixture of 2-nitro-3-methoxybenzonitrile (2.00 g, 0.0112 mol) and LiCl (1.43 g, 0.034 mol) in DMF (18.7 ml) was heated to reflux. The reaction is monitored by TLC (1:1 hexane:ethyl acetate). When the starting material has disappeared (approximately 3 hours), the reaction is cooled and 56 ml of 2.5N NaOH is added. The solution is extracted with diethyl ether. The aqueous layer is acidified with 100 ml of 2N HCl, then extracted well with ethyl acetate. The organic layer is washed with brine, dried ($Na_2SO_4$), and filtered. Concentration on a rotary evaporator yields 2-nitro-3-hydroxybenzonitrile N,N-dimethylformyl hemiacetal. This product is passed through a pad of silica gel (2:1 ethyl acetate:hexane) to yield 2-nitro-3-hydroxybenzonitrile, 1.31 g (0.00799 mol, 71%).

$^1$H NMR: δ, DMSO 7.49–7.72 (3H, aromatic series of m), 12.0 (1H, bs).

A parr bottle was charged with palladium on activated carbon (5%, 0.196g). A solution of 2-nitro-3-hydroxybenzonitrile (1.31 g, 0.008 mol) in 40 ml of ethanol was added. The reaction mixture was placed under 25 psi of hydrogen gas and shaken for 1 hour. TLC (1:1 hexane:ethyl acetate) shows that no starting material remained. The mixture was filtered through Celite® and evaporated to yield 2-amino-3-hydroxybenzonitrile, 1.01 g (0.0075 mol, 94%).

$^1$H NMR: δ, DMSO 6.00–6.14 (2H, aromatic series of m), 7.15 (1H, d, J 8.5), 10.3 (1H, bs)

MS: (EI) m+@m/z 134

A solution of 2-amino-3-hydroxybenzonitrile (1.00 g, 0.0075 mol) and diethyl squarate (1.10 ml, 0.0075 mol) in dry ethanol (20 ml) was heated at 85° C. for three days. During the course of the reaction, a tan precipitate forms. The solid is filtered through a Buchner funnel, washed with cold ethanol, adsorbed on silica gel, and flash chromatographed using hexane/ethyl acetate (2:1) as the eluant to give 3-ethoxy-4-(2-hydroxy-6-cyanophenyl)amino-3-cyclobutene-1,2-dione, 0.50 g (0.0019 mol, 26%).

$^1$H NMR: δ, DMSO 1.4 (3H, t, J 8.9), 4.7 (2H, q, J 8.9), 7.2–7.4 (3H, aromatic series of m), 10.7 (1H, s), 10.8 (1H, s)

MS: (EI) m+m/z @258.

A mixture of 3-ethoxy-4-(2-hydroxy-6-cyanophenyl)amino-3-cyclobutene-1,2-dione (0.250 g, 0.00097 mol) and (R)-2,2,1-trimethylpropylamine (0.2M in ethanol, 9.7 ml, 0.0019 mol) was stirred at room temperature for two days. TLC (2:1 ethyl acetate:hexane) indicates a loss of starting material. The reaction is evaporated on a rotary evaporator. The residue is taken up in ethyl acetate and extracted well with 0.25N HCl. The organic layer is washed once with distilled water, dried ($Na_2SO_4$), and evaporated to a solid. The solid is collected and washed with diethyl ether with several drops of ethyl acetate to give 3-[(R)-2,2,1-trimethylpropylamino]-4-(2-hydroxy-6-cyanophenyl)amino-3-cyclobutene-1,2-dione, 0.230 g (0.00073 mol, 76%)

$^1$H NMR: δDMSO 0.91 (9H, s), 1.17 (3H, d, J 7.25), 3.98 (3H, aromatic series of m), 7.5 (1H, d, J 9.66), 9.33 (1H, bs), 10.75 (1H, bs)

MS: (EI) m+@m/z 313.

EXAMPLE 5

3-(Tert-amylamino)-4-(2-hydroxy-6-cyanophenyl)amino-3-cyclobutene-1,2-dione

A mixture of 3-ethoxy-4-(2-hydroxy-6-cyanophenyl)amino-3-cyclobutene-1,2-dione (0.250 g, 0.00097 mol) and tert-amylamine (1.13 ml, 0.0097 mol) was stirred in enough $CH_2Cl_2$ to form a solution at room temperature for two days. During this time a precipitate forms. The reaction solvent is evaporated on a rotary evaporator, the residue is taken up in ethyl acetate and extracted well with 0.25N HCl. The organic layer is washed once with distilled water, dried ($Na_2SO_4$), and evaporated to a solid. The solid is collected and gives 3-(tert-amylamino)-4-(2-hydroxy-6-cyanophenyl)amino-3-cyclobutene-1,2-dione, 0.135 g (0.00045 mol, 46%).

$^1$H NMR:δDMSO 0.88 (3H, t, 7.5), 1.37 (6H, s), 1.72 (2H, q, J 7.5), 7.18–7.24 (aromatic series of m), 7.76 (1H, bs), 9.47 (1H,bs), 10.75 (1H, bs)

MS: (EI) m+@m/z 299

EXAMPLE 6

3-(2-Hydroxy-6-methylphenylamino)-4-(2,2,1-trimethylpropylamino)-cyclobut-3-ene-1 2-dione A solution of 2-amino-3-methylphenol (3.6 g, 29.2 mmol) and diethyl squarate (5 g, 29.4 mmol) in dry ethanol (80 mL) was heated to reflux for two days, then allowed to stand at room temperature for 48 hours. The reaction mixture was concentrated under reduced pressure and the resulting residue was suspended in ethyl acetate (50 mL). Hexane (50 mL) was added to produce a slurry, which was filtered, and rinsed with three portions of hexane:ethyl acetate (1:1). The resulting solid was suspended in dichloromethane (200 mL) and methanol (20 mL), stirred at room temperature for 30 minutes, and filtered. The precipitate was suspended in hot dichloromethane, filtered hot, and dried to give 3-ethoxy-4-(2-hydroxy-6-methylphenylamino)-cyclobut-3-ene-1,2-dione, 1.56 g (6.3 mmol, 22%).

$^1$H NMR: δDMSO 1.10 –1.52 (3H, two overlapping multiplets, rotamers), 2.12 (3H, s), 2.50 (3H, s), 4.30–4.80 (2H, two overlapping multiplets, rotamers), 6.62 (1H, d), 6.70 (1H, d), 7.00 (1H, t), 9.62 (1H, s), 9.90 and 10.0 (1H, two overlapping brs, rotamers)

3-Ethoxy-4-(2-hydroxy-6-methyl-phenylamino)-cyclobut-3-ene-1,2-dione (0.4 g, 1.62 mmol) and (R)-2-amino-3,3-dimethylbutane (16 mL of a 0.2M solution in absolute ethanol, 3.20 mmol) in dichloromethane (4 mL) was heated at 80° C. for 4 hours. The reaction mixture was cooled, concentrated under reduced pressure, and the resulting residue was triturated with hexane:ethyl acetate (1:1) to produce a solid, which was filtered and rinsed with hexane-:ethyl acetate (1:1). Chromatography with 10% methanol in dichloromethane gave (R)-3-(2-hydroxy-6-methylphenylamino)-4-(2,2,1-trimethylpropyl-amino)-cyclobut-3-ene-1,2-dione, 0.24 g (0.79 mmol, 49%).

$[\alpha]^{25}_D$ =+10.25° (6.4 mg/mL, DMSO).

$^1$H NMR: δDMSO 0.89 (9H, br s), 1.13 (3H, br m), 2.15 (3H, s), 3.95 (1H, br m), 6.67 (1H, d, J=7.2), 6.72 (1H, d, J=7.2), 6.96 (1H, t, J=7.8), 7.15 (1H, br s), 8.75 (1H, br s), 9.70 (1H, br s)

MS: (EI) m+@m/z 302

(S)-3-(2-hydroxy-6-methylphenylamino)-4-(2,2,1-trimethylpropylamino)-(cyclobut-3-ene-1,2-dione is produced by the same method by substituting (S)-2-amino-3,3-dimethylbutane for the (R)-2-amino-3,3-dimethylbutane employed in the preceding paragraph.

EXAMPLE 7

3-tert-Butylamino-4-(2-hydroxy-6-methyl-phenylamino)-cyclobut-3-ene-1,2-dione

3-Ethoxy-4-(2-hydroxy-6-methyl-phenylamino)-cyclobut-3-ene-1,2-dione (0.4 g, 1.62mmol) in t-butylamine (4.8mL) and dichloromethane (4.8mL) was allowed to stand at room temperature for 7 days. The slurry was filtered, rinsed with ethyl acetate, and dried. Chromatography with 10% methanol in dichloromethane, followed by trituration with 5% ethyl acetate in hexane gave 3-tert-butylamino-4-(2-hydroxy-6-methyl-phenylamino)-cyclobut-3-ene-1,2-dione, 0.18 g (0.66 mmol, 41%).

$^1$H NMR: δ, DMSO 1.41 (9H, br s), 2.14 (3H, s), 6.66 (1H, d, J=7), 6.71 (1H, d, J=7), 6.95 (1H, t, J=7), 7.60 (1H, br s), 8.78 (1H, br s), 9.70 (1H, br s)

MS: (EI) m+@m/z 274

The smooth muscle relaxing activity of the compounds of this invention was established in accordance with standard pharmaceutically accepted test procedures with representative compounds as follows:

Sprague-Dawley rats (150–200 g) are rendered unconscious by $CO_2$ asphyxiation and then euthanized by cervical dislocation. The bladder is removed into warm (37 deg. C.) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 μM carbachol. The carbachol is then washed out and the tissue allowed to relax to its resting level of activity. Following a further 30 minute period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity. The ($IC_{50}$ concentration) is calculated from this concentration-response curve. The maximum percentage inhibition of contractile activity evoked by a test compound is also recorded for concentrations of test compound less than or equal to 30 μM.

The results of this study are shown in Table I.

TABLE I

Inhibition of Contractions in Isolated Rat Bladder Strips

| Compound | n | $IC_{50}$ (μM) |
| --- | --- | --- |
| Example 1 | 2 | 3.1 ± 0.55 |
| Example 2 | 2 | 0.54 ± 0.02 |
| Example 3 | 2 | 6.05 ± 3.95 |
| Example 4 | 2 | 1.8 ± 0.2 |
| Example 5 | 4 | 0.45 ± 0.07 |
| Example 6 | 6 | 2.51 ± 1.22 |
| Example 7 | 4 | 6.39 ± 5.2 |

Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally parenterally, or by aspiration to a patient in need thereof.

What is claimed is:

1. A compound of the formula

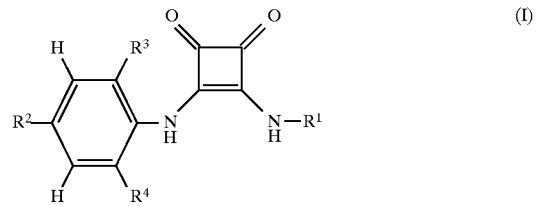

wherein:

$R^1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

and one of $R^2$, $R^3$ and $R^4$ is hydroxyl and the other two are, independently, H, CN, halogen, alkyl of 1 to 3 carbon atoms or hydroxyl;

or a pharmaceutically acceptable salt thereof.

2. A compound of claim 1 in which $R^1$ is straight chain alkyl of 1 to 10 carbon atoms, branched chain alkyl of 3 to 10 carbon atoms or fluoroalkyl of 1 to 10 carbon atoms;

and one of $R^2$, $R^3$ and $R^4$ is hydroxyl and the other two are, independently, H, CN, halogen, alkyl of 1 to 3 carbon atoms or hydroxyl;

or a pharmaceutically acceptable salt thereof.

3. The compound of claim 1 which is 3-(tert-butylamino)-4-(2-hydroxy-4-cyanophenyl)amino-3-cyclobutene-1,2-dione or a pharmaceutically acceptable salt thereof.

4. The compound of claim 1 which is 3-(tert-amylamino)-4-(2-hydroxy-4-cyanophenyl)amino-3-cyclobutene-1,2-dione or a pharmaceutically acceptable salt thereof.

5. The compound of claim 1 which is 3-(2,2,1-trimethylpropylamino)-4-(2-hydroxy-4-cyanophenyl)amino-3-cyclobutene-1,2-dione or a pharmaceutically acceptable salt thereof.

6. The compound of claim 1 which is 3-(2,2,1-trimethylpropylamino)-4-(2-hydroxy-6-cyanophenyl)amino-3-cyclobutene-1,2-dione or a pharmaceutically acceptable salt thereof.

7. The compound of claim 1 which is 3-(tert-amylamino)-4-(2-hydroxy-6-cyanophenyl)amino-3-cyclobutene-1,2-dione or a pharmaceutically acceptable salt thereof.

8. The compound of claim 1 which is 3-(2-hydroxy-6-methylphenylamino)-4-(2,2,1trimethylpropylamino)-cyclobut-3-ene-1,2-dione or a pharmaceutically acceptable salt thereof.

9. The compound of claim 1 which is 3-tert-butylamino-4-(2-hydroxy-6-methylphenylamino)-cyclobut-3-ene-1,2-dione or a pharmaceutically acceptable salt thereof.

10. A pharmaceutical composition of matter comprising a compound of the formula:

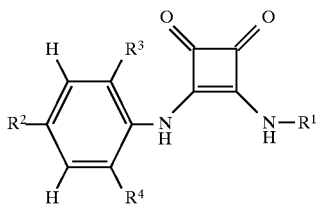 (I)

wherein:
R¹ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

and one of R², R³ and R⁴ is hydroxyl and the other two are, independently, H, CN, halogen, alkyl of 1 to 3 carbon atoms or hydroxyl;

or a pharmaceutically acceptable salt thereof and a pharmaceutically acceptable carrier therefor.

11. A method for reducing the adverse effects of smooth muscle contractions which comprises administering, orally or parenterally, to a patient in need thereof, a compound of the formula:

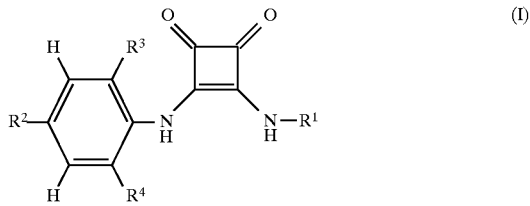 (I)

wherein:

R¹ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

and one of R², R³ and R⁴ is hydroxyl and the other two are, independently, H, CN, halogen, alkyl of 1 to 3 carbon atoms or hydroxyl;

or a pharmaceutically acceptable salt thereof.

12. The method of claim 11 in which the smooth muscle adversely contracting causes urinary incontinence.

13. The method of claim 11 in which the smooth muscle adversely contracting causes irritable bowel syndrome.

* * * * *